(12) United States Patent
Walker et al.

(10) Patent No.: US 7,034,933 B2
(45) Date of Patent: Apr. 25, 2006

(54) SYSTEM AND METHOD FOR IN VITRO ANALYSIS OF THERAPEUTIC AGENTS

(75) Inventors: Dwight Sherod Walker, Durham, NC (US); Mark Austin Patrick, Durham, NC (US)

(73) Assignee: Smithkline Beecham Corporation, Philadelphia, PA (US)

( * ) Notice: Subject to any disclaimer, the term of this patent is extended or adjusted under 35 U.S.C. 154(b) by 419 days.

(21) Appl. No.: 10/451,868

(22) PCT Filed: Jan. 25, 2002

(86) PCT No.: PCT/US02/02223

§ 371 (c)(1),
(2), (4) Date: Jun. 25, 2003

(87) PCT Pub. No.: WO02/059599

PCT Pub. Date: Aug. 1, 2002

(65) Prior Publication Data

US 2004/0061854 A1     Apr. 1, 2004

Related U.S. Application Data

(60) Provisional application No. 60/264,363, filed on Jan. 26, 2001.

(51) Int. Cl.
*G01N 1/10* (2006.01)
(52) U.S. Cl. .................................... 356/246; 356/319
(58) Field of Classification Search ............ 356/319, 356/432, 436, 246, 338; 422/82.05
See application file for complete search history.

(56) References Cited

U.S. PATENT DOCUMENTS 4,684,805 A * 8/1987 Shu-Ti Lee et al. ......... 250/343
5,368,725 A * 11/1994 Bredeweg et al. .......... 422/101

(Continued)

FOREIGN PATENT DOCUMENTS

WO          9746866        12/1997

OTHER PUBLICATIONS

Evans, JJ et. al.; "The effects of lidocaine and quinidine on impulse propagation across the canine purkinje-muscle junction during combined hyperkalemia, hypoxia, and acidosis"; Circulation Research; Aug. 1984; vol. 55; No. 2; 185-196.

*Primary Examiner*—Gregory J. Toatley, Jr.
*Assistant Examiner*—Juan D. Valentin, II
(74) *Attorney, Agent, or Firm*—Robert J. Smith

(57) ABSTRACT

A system and method for in vitro analysis of therapeutic agents comprising a reservoir adapted to hold a therapeutic agent, a first flow cell having a first cell chamber adapted to receive at least a first sample of the therapeutic agent, a second flow cell having a second cell chamber adapted to receive at least a second sample of the therapeutic agent, the first flow cell having a first path length ($b_e'$) and the second flow cell having a second path length ($b_e''$), the first path length being substantially equal to a sensitivity factor (f)× $b_e''$, a membrane chamber having a biological cell membrane therein adapted to receive at least a third sample of the therapeutic agent, the membrane chamber being further adapted to detect the membrane potential of the biological cell membrane; and spectroscopic detection means for detecting the spectral characteristics of the first and second therapeutic agent samples.

23 Claims, 4 Drawing Sheets

U.S. PATENT DOCUMENTS

| | | | |
|---|---|---|---|
| 5,695,719 A * | 12/1997 | Lynggaard et al. | 436/174 |
| 5,815,276 A * | 9/1998 | Fry | 356/437 |
| 6,006,585 A * | 12/1999 | Forster | 356/437 |
| 6,580,507 B1 * | 6/2003 | Fry et al. | 356/436 |

* cited by examiner

SYSTEM AND METHOD FOR IN VITRO ANALYSIS OF THERAPEUTIC AGENTS

This application claims the benefit of 60/264,363, filed Jan. 26, 2001.

FIELD OF THE PRESENT INVENTION

The present invention relates generally to electrophysiologic assessment of therapeutic agents. More particularly, the invention relates to a system and method for in vitro assessment of therapeutic agents that employs spectroscopic means for accurate determination of the agent's concentration.

BACKGROUND OF THE INVENTION

The potential of cardiovascular and non-cardiovascular therapeutic agents or drugs to cause prolongation of the QT (i.e., cardiac repolarization time between two ventricular sequences) interval of the electrocardiogram has been, and continues to be, a significant factor in the development of new therapeutic agents. Indeed, it is well established that a wide range of non-cardiovascular therapeutic agents that are not expected on the basis of their mechanism of action to prolong QT can produce a substantial number of serious cardiac events. Such agents belong to different pharmacological classes, such as psychotropic drugs (e.g., tricyclic-amitriptiline and tetracyclic antidepressants, phenothiazine derivatives, haloperidol, pimozide, risperidone and sertindole), prokinetic (e.g., cisapride), antimalarial medicines (e.g., halofantrine, quinine, and chloroquine), antibiotics belonging to several chemical classes (e.g., azithromycin, erythromycin, clarithromycin, spiramycin, pentamidine, trimethoprim-sulfamethoxazole and sparfloxacin), antifungal agents (e.g., ketoconazole, fuconazole and itraconazole), agents for treating urinary incontinence (e.g., terodiline), and certain histamine $H_1$-receptor antagonist (e.g., astemizole, terfenadine and diphenhydramine).

These therapeutic agents, in certain very rare instances, can trigger life-threatening polymorphic ventricular tachycardias, such as torsade de pointes, often in the presence of additional factors favoring, directly or indirectly, proarrhythmic events. The relevant factors include congenital or acquired long-QT syndrome, ischemic heart disease, congestive heart failure, severe hepatic or renal dysfunction, bradycardia, electrolyte imbalance (e.g., hypokalemia due to diuretic treatment, hypomagnesemia, hypocalcemia, acidosis and intracellular $Ca^{++}$ loading), intentional or accidental overdose, and concomitant treatment with ion channel blocking drugs or agents that inhibit the drug detoxification processes.

Several preclinical techniques have thus been employed to evaluate the cardiovascular effects of proposed therapeutic agents. The noted techniques to determine concentration of proposed therapeutic agents primarily comprise high performance liquid chromatography (HPLC) or other analytical assays that are generally limited to higher therapeutic agent concentrations unless pre-concentration or large volumes are employed.

It is, however, well known that the noted physiological analytical assays are often laborious, expensive, time consuming and frustrated by technical problems. Further, HPLC and/or assays may require hours to days to analyze samples and process data depending on the complexity and number of samples.

It is therefore an object of the present invention to provide a system and method for high-speed, economical in vitro analyses of therapeutic agents.

It is another object of the present invention to provide a system and method for in vitro analysis of low concentration therapeutic agents.

It is yet another object of the present invention to provide a system and method for correlating the electrophysiological effects of a proposed therapeutic agent over a broad concentration range.

SUMMARY OF THE INVENTION

In accordance with the above objects and those that will be mentioned and will become apparent below, in a preferred embodiment, the system for in vitro analysis of therapeutic agents in accordance with this invention comprises a reservoir adapted to hold a therapeutic agent, a first flow cell having a first cell chamber adapted to receive at least a first sample of the therapeutic agent, a second flow cell having a second cell chamber adapted to receive at least a second sample of the therapeutic agent, the first flow cell having a first path length ($b_e'$) and the second flow cell having a second path length ($b_e''$) the first path length being substantially equal to a sensitivity factor $(f) \times b_e''$, a membrane chamber having a biological cell membrane therein adapted to receive at least a third sample of the therapeutic agent, the membrane chamber being further adapted to detect the membrane potential of the biological cell membrane, and spectroscopic detection means for detecting the spectral characteristics of the first and second therapeutic agent samples.

The method for in vitro analysis of therapeutic agents in accordance with the invention preferably comprises the steps of (i) introducing a first sample of a therapeutic agent into a first flow cell having a first path length ($b_e'$), (ii) introducing a second sample of the therapeutic agent into a second flow cell having a second path length ($b_e''$), the first path length ($b_e'$) being substantially equal to a sensitivity factor $(f) \times b_e''$, (iii) introducing a third sample of the therapeutic agent into membrane chamber means having a biological cell membrane disposed therein, (iv) measuring the absorption spectrum of the first therapeutic agent sample by transmitting a given wavelength of a first light into the first flow cell, (v) measuring the absorption spectrum of the second therapeutic agent sample by transmitting a given wavelength of a second light into the second flow cell, and (vi) detecting the membrane potential of said biological cell membrane.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

The method and system of the present invention substantially reduces or eliminates the drawbacks and shortcomings associated with prior art electrophysiologic assessment of therapeutic agents. As discussed in detail below, the system generally includes a plurality of flow cells, spectroscopic means in communication with the flow cells, membrane chamber means and flow passage means for introducing the subject therapeutic agent(s) to the flow cells and membrane chamber means.

By the term "therapeutic agent", as used herein, it is meant to mean and include active ingredients, components or elements of a pharmaceutical composition, drugs and medicaments.

Cardiac action potential (or membrane potential) is generally defined as the pattern of electrical activity that is associated with excitable biological cells (e.g., heart cells). It is the result of numerous, distinct, successively activated currents generated by the passage of biologically important ions ($Na^+$, $Ca^{++}$ and $K^+$) through specialized membrane structures such as ionic pumps and exchangers and, most importantly, voltage-gated ion channels. These currents are considered to be depolarizing when they carry extracellular positive charges into the cell and to be repolarizing when they carry positive charges to the cell exterior.

Therapeutic agents that modify the normal flux of ions through channels can, and in many instances will, modify certain aspects of the membrane potential and, thus, affect cardiac function. Indeed, blockers of $Na^+$ channels reduce the rate of rise of the membrane potential (Vmax) and can produce disturbances in cardiac conduction, which, if severe, may be life threatening. Agents that decrease the rate of Na-current inactivation and increase residual Na-current can prolong the duration of the action potential (ADP), prolong the QT interval and thus may trigger torsades de pointes arrhythmias. Blockers of $Ca^{++}$ channels generally decrease ADP, reduce the rate of A-V conduction and produce cardiac depression, whereas $Ca^{++}$ channel-activators prolong ADP and may cause arrhythmias. Finally, $K^+$ channel-blockers prolong ADP and QT and can provoke arrhythmias, whereas $K^+$ channel-activators shorten ADP and can also trigger arrhythmia.

Thus, an effective indicator (or parameter) of possible adverse cardiac effects of a proposed therapeutic agent is the change in membrane potential (i.e., membrane resting potential) resulting from the introduction or exposure to the therapeutic agent. Indeed, the noted parameter is often deferred to in conventional physiological assessments of proposed therapeutic agents (or drug candidates). As discussed in detail below, the noted parameter is also employed in the present invention to assess the potential physiological effect(s) of a therapeutic agent.

Figure 1:
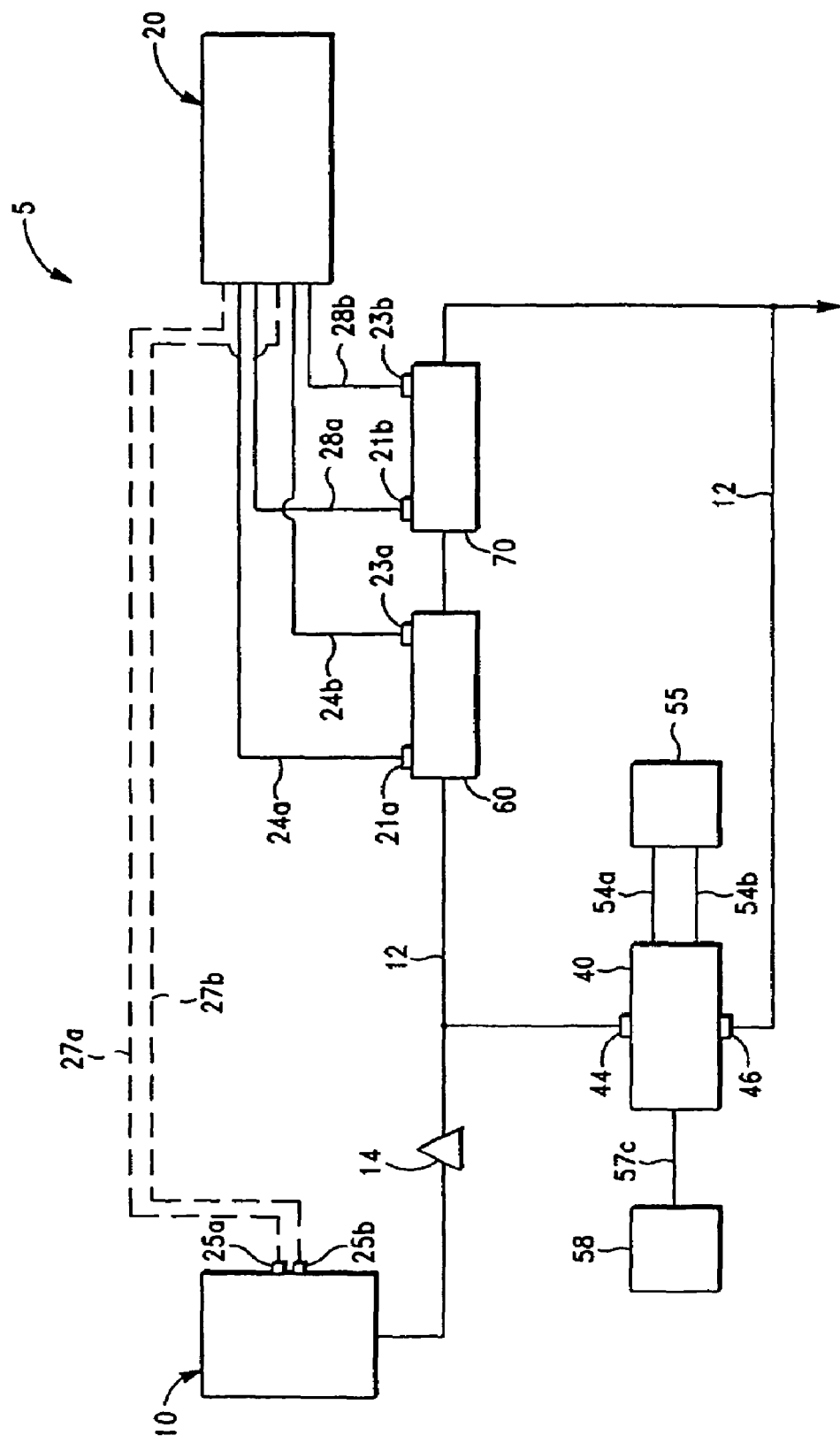
FIG. 1 is a schematic illustration of one embodiment of the in vitro spectroscopic system for analysis of therapeutic agents according to the invention.

Referring now to FIG. 1, there is shown a schematic illustration of one embodiment of the in vitro analysis system 5 of the invention. As illustrated in FIG. 1, the system 5 preferably includes reservoir means (e.g. reservoir) 10, optic based spectroscopic detection means 20, a plurality of flow cells, preferably first and second flow cells 60, 70, membrane chamber means 40 and flow passage means 12.

According to the invention, the reservoir means 10 is designed and adapted to store at least one therapeutic agent in diluent. As will be appreciated by one having ordinary skill in the art, various capacity (and configuration) reservoir means 10 may be employed within the scope of the invention. In a preferred embodiment of the invention, the capacity of the reservoir means 10 is in the range of 1 to 2000 ml.

The reservoir means 10 is further designed and adapted to receive the flow passage means 12 of the invention, which preferably comprises substantially non-adsorbing tubing (e.g., stainless steel, PEEK®. As illustrated in FIG. 1, pump means 14 is also provided to facilitate flow of the therapeutic agent (i.e., therapeutic agent sample or samples) from the reservoir means 10 to and through the first and second flow cells 60, 70. The pump means 14 is in communication with the flow passage means 12 and is preferably disposed between the reservoir means 10 and the flow cells 60, 70. According to the invention, the pump means 14 is capable of achieving a sample flow rate in the range of $\leq 0.5$ to $\geq 10$ ml/min., more preferably, in the operating range of approximately 2 to 5 ml/min.

As will be appreciated by one having ordinary skill in the art, various pump means 14 may be employed within the scope of the invention to provide the noted sample flow rate(s). In a preferred embodiment, the pump means 14 comprises a peristaltic pump.

Figure 2:
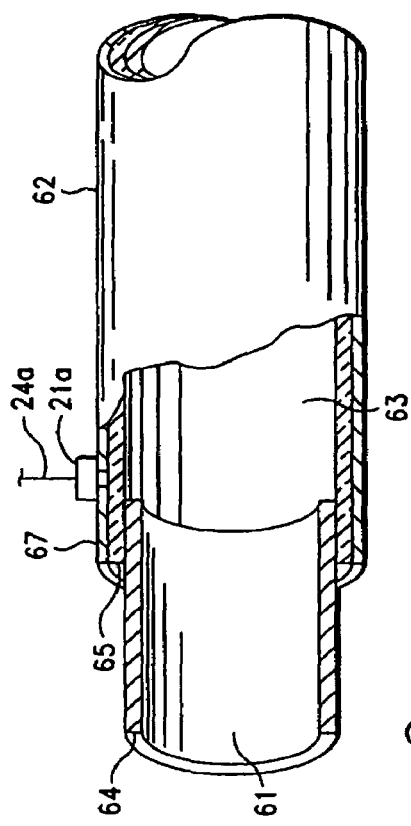
FIG. 2 is a partial section plan view of one embodiment of a flow cell according to the invention.
Figure 2:
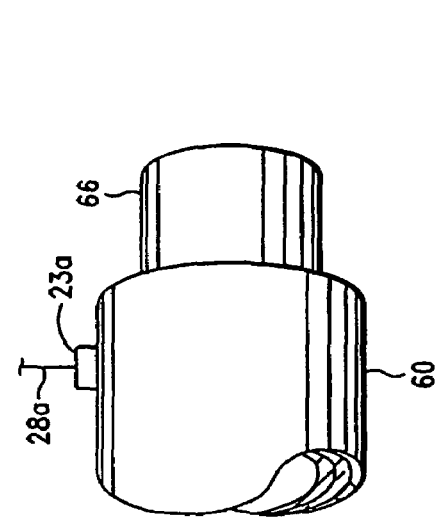

Referring now to FIG. 2, there is shown one embodiment the first flow cell 60 of the invention. For simplicity, only the first flow cell 60 will be illustrated and described. However, it is to be understood that the second flow cell 70 of the noted embodiment is similarly constructed and the description of the first flow cell 60 is equally applicable to each flow cell 60, 70.

As illustrated in FIG. 2, the flow cell 60 preferably includes a substantially tubular body 62 having an inlet port 64, an outlet port 66 and a cell chamber, designated generally 63, disposed therein that is adapted to receive a therapeutic agent sample. According to the invention, the inlet and outlet ports 64, 66 and cell chamber 63 define a flow passage 61.

As will be appreciated by one having ordinary skill in the art, various flow cell body 62 materials may be employed within the scope of the invention. In a preferred embodiment of the invention, the body 62 of each flow cell 60, 70 includes a core comprising a polymer, silica, chalcogenide or other like materials and cladding 67 disposed on the outer surface of the core comprising a polymer or doped silica or other like materials (see FIGS. 2 and 4).

According to the invention, the first flow cell 60 further includes first light transmission means 21a adapted to provide a given wavelength of excitation light or radiation (and/or a given range thereof) to the flowable therapeutic agent present in the first flow cell chamber 63 (i.e., first sample) and first light detection means 23a for detecting the transmitted light from the first sample. The second flow cell 70 similarly includes second light transmission means 21b adapted to provide a given wavelength of excitation light (and/or a given range thereof) to the sample present in the cell chamber of the second flow cell 70 (i.e., second sample) and second light detection means 23b for detecting the transmitted light from the second sample.

Figure 3:
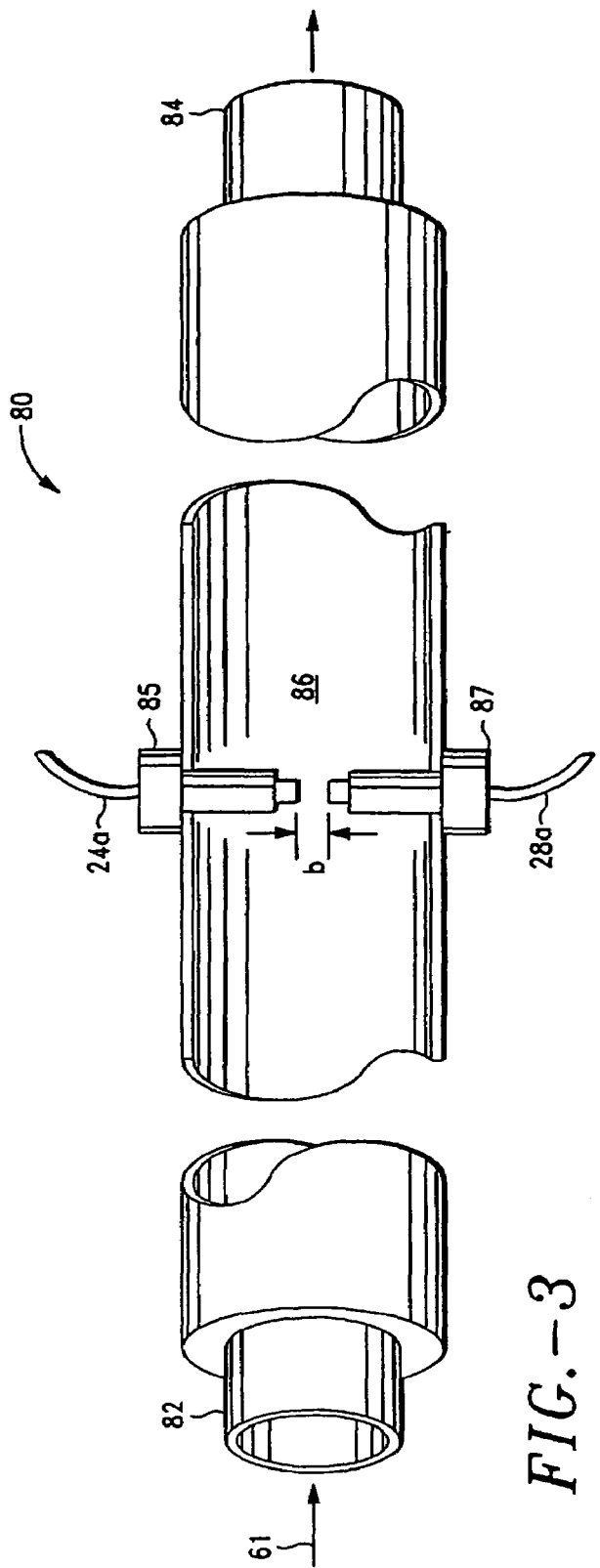
FIG. 3 is a partial section plan view of an additional embodiment of a flow cell according to the invention.

Referring now to FIG. 3, there is shown another embodiment of a flow cell 80 of the invention. The flow cell 80 similarly includes an inlet port 82, an outlet port 84 and a cell chamber, designated generally 86, disposed there between that is similarly adapted to receive a therapeutic agent sample.

The flow cell 80 further includes first light transmission means 85 adapted to provide a given wavelength of excitation light or radiation to the flowable therapeutic agent present in the flow cell chamber 86 (i.e., first sample) and first light detection means 87 for detecting the transmitted light from the first sample.

It is well known that when each sample passes through a respective flow cell chamber (e.g., 63) the amount of excitation light transmitted into and through the cell chamber 63 decreases in accordance with Beer's Law, i.e., $$A = \frac{I}{I_o} = 10^{-\alpha bc} \qquad \text{Eq. 1}$$

where:
A=absorbance;
I=power of transmitted radiation;
$I_o$=power of incident radiation;
c=molar absorptivity of the sample;
c=sample concentration (moles/liter); and
b=path length of the light in the chamber (cm.)

The absorbance (A) is thus defined as the product of $\alpha bc$. According to Beer's Law, absorbance (A) is also proportional to both the sample concentration (c) and path length (b).

As will be appreciated by one having ordinary skill in the art, the path length (b) is generally deemed a "straight path length" that is applicable in light transmission/detection configurations such as that illustrated in FIG. 3. It will further be appreciated by one having skill in the art that the noted Beer's Law relationship is similarly applicable for the light transmission/detection configuration (i.e., 21a, 23a) of the cylindrical flow cell 60 of the invention (see FIG. 2), which employs attenuated total reflection.

Figure 4:
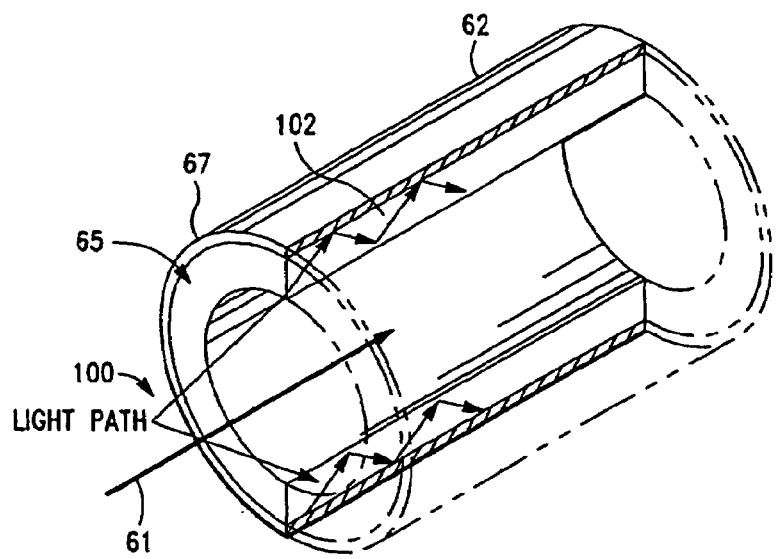
FIG. 4 is a schematic illustration of a flow cell body showing the attenuated light path according to the invention.

Referring to FIG. 4, it is well known that when radiation (or light), designated generally 100, undergoes total internal reflection 102, it actually penetrates a fraction of a wavelength into the medium (or sample) beyond the reflecting surface. The penetration depth is generally denoted $d_p$.

Since the penetration depth $d_p$ is defined as a unit length/reflection, an equivalent path length ($b_e$) can thus be derived as follows:

$$b_e = d_p \times R \times L \qquad \text{Eq.2}$$

where:
$d_p$=penetration depth per reflection;
R=number of reflections per unit length; and
L=length of tube or cell.

The equivalent path length ($b_e$) can then be employed in Eq.1 to derive the absorbance of a respective sample (A).

As will further be appreciated by one having ordinary skill in the art, the effective path length ($b_e$) of a respective flow cell 60, 70 is directly dependent on the length of the flow cell body 62. Thus, the length of each flow cell 60, 70 can be tailored to provide different path lengths.

It can further be deduced from Beer's Law that if the absorbance range of the spectroscopic means (e.g., spectrophotometer) is fixed, which is a common element of conventional spectroscopic means, the path length (b or $b_e$) must be increased for lower molar absorptivity ($\alpha$) or lower concentration (c). However, as is well known in the art, the response band generally associated with a larger path length is undesirably narrow and, hence, limited.

It is also well known in the art that a broader response band can be achieved by employing two (2) flow cells having different path lengths ($b_e'$, $b_e''$). The typical path lengths generally range from 0.1 to 100 cm.

Applicants have however found that an optimum dynamic (i.e., substantially linear) response range can be achieved if $b_e'$ is substantially equal to $b_e''$ ×a sensitivity factor (f). According to the invention, the sensitivity factor (f) preferably has a value in the range of 1 to 100. More preferably, f has a value in the range of 1 to 20.

Figure 5:
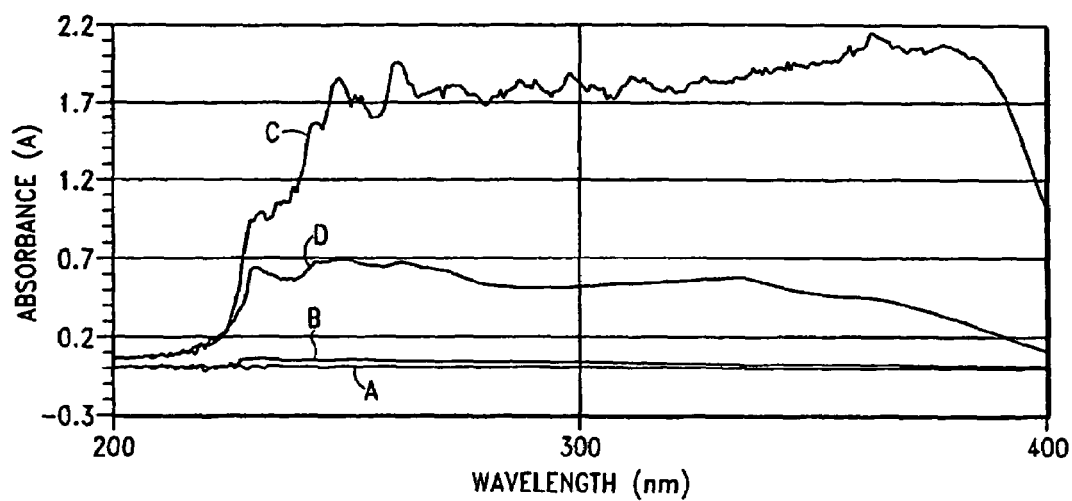
FIG. 5 is a graphical illustration of absorbance spectra of a pharmaceutical composition having a low concentration therapeutic agent and a high concentration therapeutic agent.

Referring to FIG. 5, there are shown absorbance spectra of a low concentration therapeutic agent (i.e., ~18 ng/ml) and a high concentration therapeutic agent (i.e., ~3800 ng/ml). The noted absorbance spectra was derived with a first flow cell having a path length of approx. 5 cm and a second flow cell having a path cell of approx. 50 cm (i.e., f=10).

Referring to Curve A, it can be seen that a path length of 5 cm was insufficient to detect the low concentration therapeutic agent over a range of wavelengths from 200 nm to 400 nm. However, as illustrated by Curve B, the same agent was readily detectable (and quantifiable) at a path length of 50 cm.

Referring now to Curve C, it can be seen that the high concentration therapeutic agent was not quantifiable at a path length of 50 cm. However, as illustrated in Curve D, the same agent was readily detectable at a path length of 5 cm.

Accordingly, in a preferred embodiment of the invention, the first flow cell 60 has an effective path length ($b_e'$) in the range of 0.1 to 100 cm and second flow cell 70 has an effective path length ($b_e''$) in the range of 0.1 to 100 cm. More preferably, the first flow cell 60 has an effective path length ($b_e'$) in the range of approx. 5 to 50 cm and the second flow cell 70 has a path length ($b_e''$) in the range of approx. 50 to 100 cm. Applicants have found that accurate spectral characteristics of therapeutic agents having a substantially low concentration in the range of 5 to 10 ng/ml can readily be detected by virtue of the noted range of path lengths ($b_e'$, $b_e''$).

Figure 6:
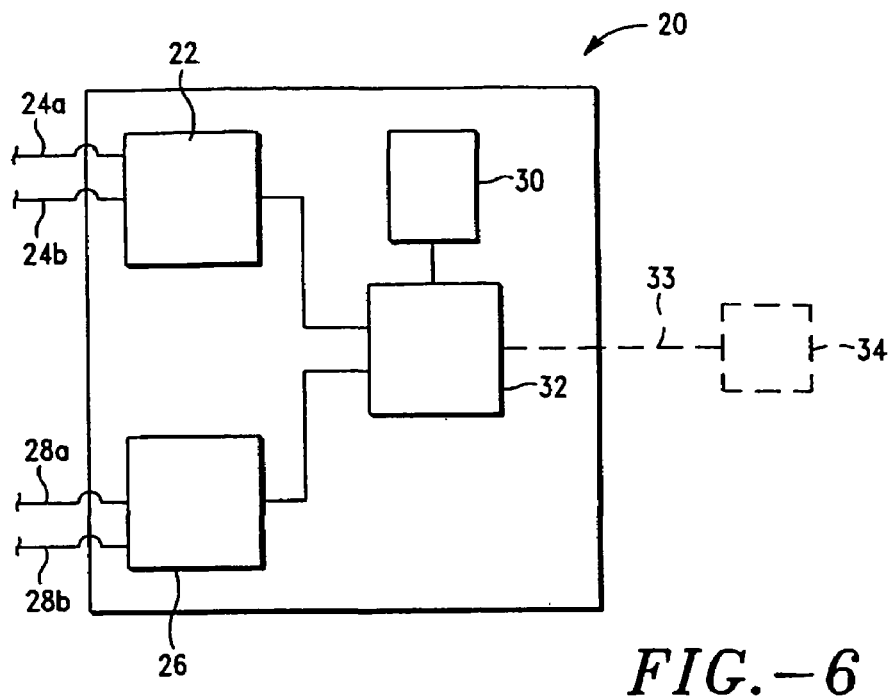
FIG. 6 is a schematic illustration of the spectroscopic means according to the invention.

Referring now to FIG. 6, in addition to the first and second light transmission means 21a, 21b and first and second light detection means 23a, 23b shown in FIG. 2, the spectroscopic means 20 of the invention further includes light source means 22 for providing the desired wavelength of light to the first and second light transmission means 21a, 21b via optical lines 24a and 24b, respectively, and analyzer means 26 for analyzing the light detected by the first and second light detection means 23a, 23b, which is communicated to the analyzer means 26 via optical lines 28a and 28b, respectively.

In additional envisioned embodiments of the invention, the reservoir means 10 also includes light transmission means 25a and light detection means 25b that are operatively connected to the spectroscopic means 20 of the invention via optical lines 27a, 27b. As will be appreciated by one having ordinary skill in the art, the reservoir means light transmission and detection means 25a, 25b provides means for simultaneously assessing and monitoring the agent contained in the reservoir means 10 and, hence, means for detecting therapeutic agent loss and ensuring that the samples analyzed in the flow cells 60, 70 are representative of the source therapeutic agent contained in the reservoir means 10.

As illustrated in FIG. 6, the spectroscopic means 20 further preferably includes memory means 30 for storing at least the detected spectroscopic characteristics of the first and second samples (and source agent contained in the reservoir means 10) and the control parameters for the spectroscopic means of the invention, processor means 32 for processing at least the spectroscopic characteristics of the samples (and source agent) and first display means 34 (shown in phantom) for displaying at least the spectroscopic characteristics of the samples, the source pharmaceutical agent contained in the reservoir means 10 and the "processed" spectroscopic characteristics of the samples (e.g., mean values).

As will be appreciated by one having ordinary skill in the art, various conventional light source means 22 and/or analyzer means 26 can be employed within the scope of the invention to provide a given range of wavelength of light, analyze the spectroscopic characteristics (e.g., absorption spectrum of the absorbed light) acquired by the first and second light detection means 23a, 23b and control the spectroscopic means 20 of the invention, such as the analyzers disclosed in U.S. Pat. No. 4,664,522 and the MCS-521 fiber optic UV/VIS spectrophotometer distributed by Carl Zeiss, which are incorporated by reference herein. The analyzer means 26 and/or the processor means 32 may also comprise a personal computer.

Figure 7:
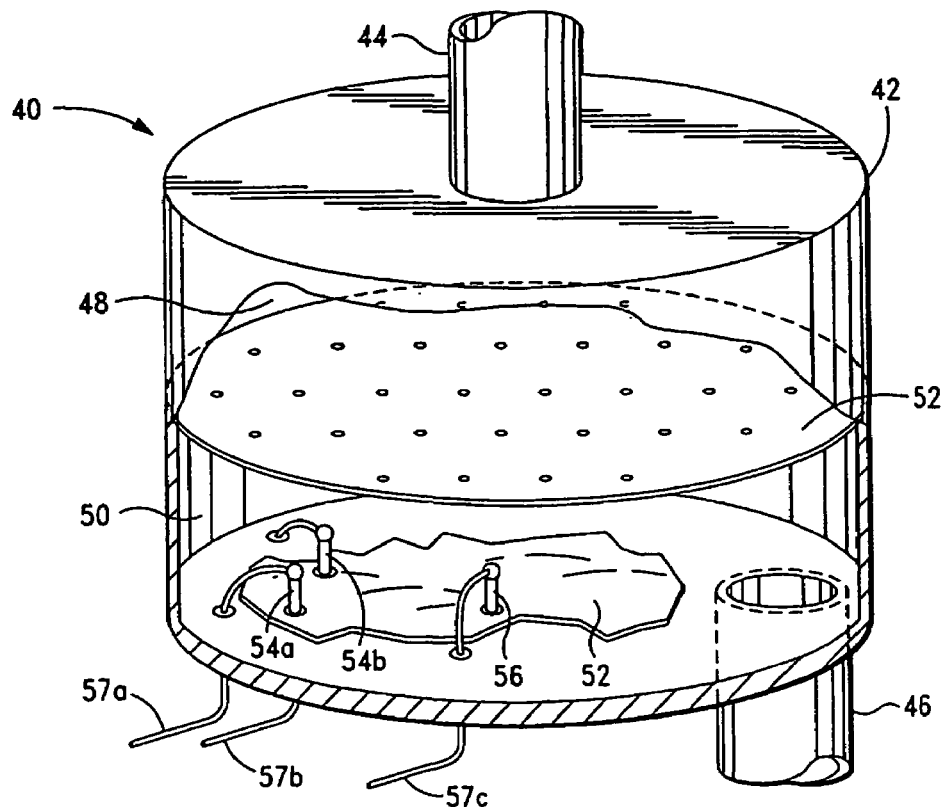
FIG. 7 is a partial section perspective view of the membrane chamber means according to the invention.

Referring now to FIG. 7, there is shown the membrane chamber means 40 of the invention. The membrane chamber means 40 includes a membrane chamber body 42 having a perfusion inlet 44, a perfusion outlet 46, a preparation well 48, a membrane well 50 and a diffuser plate 52 disposed between the preparation well 48 and membrane well 50.

As illustrated in FIG. 7, the membrane chamber means 40 further includes membrane means 52 disposed in the membrane well 50. By the term "membrane means", as used herein, it is meant to mean a biological cell membrane, including a sheet or layer of a biological organ, the ventricular muscle and/or papillary muscle, and Purkinje fibers.

In a preferred embodiment of the invention, the membrane means 52 comprises a Purkinje fiber. As is well known in the art, Purkinje fibers are often employed in electrophysiological assessments because it is believed that the major ionic currents underlying their action potentials resemble those contributing to the repolarization process of the human heart.

To assess the membrane potential of the membrane means 52, the membrane chamber means 40 further includes a plurality of electrodes. Referring to FIG. 7, at least one, preferably two, bipolar electrodes 54a, 54b are operatively connected to the membrane means 52 proximate one end thereof. The electrodes 54a, 54b are also in communication with the stimulation means 55 of the invention via leads 54a, 54b (see FIG. 1) and are adapted to provide a stimulating charge or current to the membrane means 52.

As illustrated in FIG. 7, a further electrode is also provided. In a preferred embodiment, the noted electrode comprises an intracellular microelectrode 56 that is also operatively connected to the membrane means 52.

According to the invention, the microelectrode 56 is designed and adapted to detect the membrane potential of the membrane means 52. The microelectrode 56 is preferably in communication with second display means 58 (via lead 57c) that is adapted to provide a visual display or indication of the detected potential (see FIG. 1).

Assessment of therapeutic agents in accordance with the present invention is preferably accomplished as follows: The spectroscopic means of the invention is initially calibrated by conventional means. Such means includes analysis of blank (or primary) samples as a UV reference and an analysis of calibration samples with respective blank samples as a reference.

After calibration of the spectroscopic means 20, flow of the therapeutic agent (preferably, in diluent) is initiated and the therapeutic agent is introduced into and through the flow passage means 12 via pump means 14. The therapeutic agent is then introduced into and through the flow passage 61 of the first and second flow cells 60, 70, which are preferably connected in series, and the membrane chamber means 40.

The spectroscopic characteristics of the therapeutic agent present in the first flow cell 60 (i.e., first sample) and the second flow cell 70 (i.e., second sample) are then detected (preferably, substantially simultaneously) by the above described spectroscopic means 20 of the invention. The spectroscopic characteristics are then processed and analyzed by conventional means.

In a preferred embodiment, substantially simultaneously with the spectroscopic analysis and while the therapeutic agent is present in the membrane well 50 of the membrane chamber means 40 (i.e., third sample), the membrane means 52 is subjected to an initial current via stimulating electrodes 54a, 54b. The membrane potential is then detected via electrode 56 that is displayed on the second display means 58 of the invention. The change in membrane potential is then readily determined by comparing the detected membrane potential to the potential of the membrane means 52 prior to exposure to the therapeutic agent.

As will be appreciated by one having ordinary skill in the art, the system and method of the invention, described in detail above, is also applicable to analyses of pharmaceutical compositions containing a therapeutic agent and, in particular, pharmaceutical compositions having a substantially low concentration of therapeutic agents.

SUMMARY

From the foregoing, one of ordinary skill in the art can easily ascertain that the present invention provides the following advantages:

1. High speed, highly accurate and economical (i.e., low cost) in vitro analyses of therapeutic agents.

2. High speed, efficient in vitro analyses of pharmaceutical compositions having a substantially low concentration (i.e., 5–10 ng/ml) of therapeutic agents.

3. High speed, efficient means for correlating the electrophysiological effects of a proposed therapeutic agent over a broad concentration range.

4. Means for assessing and monitoring the stability of the therapeutic agent during in vitro analyses.

5. Means for assessing and monitoring agent loss (e.g., glassware absorption and/or attachment) during in vitro analyses.

6. Means for rapidly and efficiently detecting carryover (i.e., cross-contamination) in a reservoir and/or feed lines.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A system for use in in-vitro analysis of a therapeutic agent, said system comprising:

a reservoir adapted to hold said therapeutic agent;

a first flow cell in communication with said reservoir having a first cell chamber adapted to receive at least a first sample of said therapeutic agent;

a second flow cell in communication with said reservoir having a second cell chamber adapted to receive at least a second sample of said therapeutic agent;

said first flow cell having a first path length ($b_e'$) and said second flow cell having a second path length ($b_e''$), said first path length being substantially equal to sensitivity factor (f)×$b_e''$;

a membrane chamber in communication with said reservoir having a biological cell membrane therein, said membrane chamber being adapted to receive at least a third sample of said therapeutic agent, said membrane chamber being further adapted to detect the membrane potential of said biological cell membrane; and spectroscopic detection means for detecting the spectral characteristics of said first and second therapeutic agent samples.

2. The system of claim 1, wherein said spectroscopic detection means includes first light transmission means for transmitting a first light of a given wavelength into said first cell chamber, first light detection means for detecting a first transmitted light from said first therapeutic agent sample, second light transmission means for transmitting a second light of a given wavelength into said second cell chamber and second light detection means for detecting a second transmitted light from said second therapeutic agent sample.

3. The system of claim 2, wherein said spectroscopic detection means further includes control means in communication with said first and second light transmission means and said first and second light detection means for providing said first and second lights and analyzing said first and second transmitted lights.

4. The system of claim 1, wherein said sensitivity factor has a value in the range of 1 to 100.

5. The system of claim 4, wherein said sensitivity factor has a value in the range of 1 to 20.

6. The system of claim 1, wherein said first and second path lengths are in the range of 0.1 to 100 cm.

7. The system of claim 6, wherein said first path length is in the range of 5 to 50 cm.

8. The system of claim 6, wherein said second path length is in the range of 50 to 100 cm.

9. The system of claim 1, wherein said spectroscopic detection means includes third light transmission means for transmitting a third light of a given wavelength into said reservoir and third light detection means for detecting a third transmitted light from said therapeutic agent contained in said reservoir, said third light transmission means and third detection means being in communication with said control means.

10. The system of claim 1, wherein said spectroscopic means includes first display means for displaying at least the spectroscopic characteristics of said first and second therapeutic agent samples.

11. The system of claim 1, wherein said membrane chamber means includes second display means for displaying said membrane potential of said biological cell membrane.

12. A system for use in in-vitro analysis of a therapeutic agent, said system comprising:

a reservoir adapted to receive said therapeutic agent;

a first flow cell in communication with said reservoir having a first cell chamber adapted to receive a first sample of said therapeutic agent, said first flow cell having an effective path length in the range of approximately 5–50 cm;

a second flow cell in communication with said reservoir having a second cell chamber adapted to receive a second sample of said therapeutic agent, said second flow cell having an effective path length in the range of approximately 50–100 cm;

a membrane chamber in communication with said reservoir having a biological cell membrane therein, said membrane chamber being adapted to receive a third sample of said therapeutic agent, said membrane chamber being further adapted to detect the membrane potential of said biological cell membrane; and spectroscopic detection means for detecting the spectral characteristics of said first and second therapeutic agent samples.

13. The system of claim 12, wherein said spectroscopic detection means includes first light transmission means for transmitting a first light of a given wavelength into said first cell chamber, first light detection means for detecting a first transmitted light from said first therapeutic agent sample, second light transmission means for transmitting a second light of a given wavelength into said second cell chamber and second light detection means for detecting a second transmitted light from said second therapeutic agent sample.

14. The system of claim 13, wherein said spectroscopic detection means further includes control means in communication with said first and second light transmission means and said first and second light detection means for providing said first and second lights and analyzing said first and second transmitted lights.

15. The system of claim 14, wherein said spectroscopic detection means includes third light transmission means for transmitting a third light of a given wavelength into said reservoir and third light detection means for detecting a third transmitted light from said therapeutic agent contained in said reservoir, said third light transmission means and third detection means being in communication with said control means.

16. The system of claim 15, wherein said spectroscopic means includes display means for displaying at least the spectroscopic characteristics of said therapeutic agent contained in said reservoir and said first and second therapeutic agent samples.

17. A method for in-vitro analysis of therapeutic agents, said method comprising the steps of:

introducing at least a first sample of a therapeutic agent into a first flow cell, said first flow cell having a first path length ($b_e'$);

introducing at least a second sample of said therapeutic agent into a second flow cell, said second flow cell having a second path length ($b_e''$);

said first path length ($b_e'$) being substantially equal to a sensitivity factor (f)×$b_e''$;

introducing at least a third sample of said therapeutic agent into membrane chamber means having a biological cell membrane disposed therein;

measuring the absorption spectrum of said first therapeutic agent sample by transmitting a given wavelength of a first light into said first flow cell;

measuring the absorption spectrum of said second therapeutic agent sample by transmitting a given wavelength of a second light into said second flow cell; and detecting the membrane potential of said biological cell membrane.

18. The method of claim 17, wherein said first therapeutic agent sample absorption spectrum and said second therapeutic agent sample absorption spectrum are measured substantially simultaneously.

19. The method of claim 17, wherein said sensitivity factor has a value in the range of 1 to 100.

20. The method of claim 17, wherein said sensitivity factor has a value in the range of 1 to 20.

21. The method of claim 17, wherein said first and second path lengths are in the range of 0.1 to 100.

22. The system of claim 21, wherein said first path length is in the range of 5 to 50 cm.

23. The system of claim 21, wherein said second path length is in the range of 50 to 100 cm.

* * * * *